(12) United States Patent
Laredo et al.

(10) Patent No.: US 9,864,102 B2
(45) Date of Patent: Jan. 9, 2018

(54) HYDROPHOBIC ACRYLATE-ACRYLAMIDE COPOLYMERS FOR OPHTHALMIC DEVICES

(71) Applicant: Novartis AG, Basel (CH)

(72) Inventors: Walter Laredo, Fort Worth, TX (US);
Ali E. Akinay, Southlake, TX (US);
Xuwei Jiang, Arlington, TX (US);
David Jinkerson, Benbrook, TX (US);
Vincent Nguyen, Grapevine, TX (US);
Douglas Schlueter, Azle, TX (US)

(73) Assignee: Novartis AG, Basel (CH)

( * ) Notice: Subject to any disclaimer, the term of this patent is extended or adjusted under 35 U.S.C. 154(b) by 67 days.

(21) Appl. No.: 14/967,780

(22) Filed: Dec. 14, 2015

(65) Prior Publication Data
US 2016/0170092 A1    Jun. 16, 2016

Related U.S. Application Data

(60) Provisional application No. 62/092,319, filed on Dec. 16, 2014.

(51) Int. Cl.
| | |
|---|---|
| *A61F 2/16* | (2006.01) |
| *G02B 1/04* | (2006.01) |
| *A61L 27/16* | (2006.01) |
| *A61L 27/26* | (2006.01) |
| *A61L 27/50* | (2006.01) |
| *A61L 27/52* | (2006.01) |

(52) U.S. Cl.
CPC ............... *G02B 1/041* (2013.01); *A61F 2/16* (2013.01); *A61L 27/26* (2013.01); *A61L 27/50* (2013.01); *A61L 27/52* (2013.01); *A61L 2430/16* (2013.01)

(58) Field of Classification Search
None
See application file for complete search history.

(56) References Cited

U.S. PATENT DOCUMENTS

| | | |
|---|---|---|
| 3,162,676 A | 12/1964 | Goldberg et al. |
| 3,299,173 A | 1/1967 | Roselli |
| 4,304,895 A | 12/1981 | Loshaek |
| 4,528,311 A | 7/1985 | Beard et al. |
| 4,612,358 A | 9/1986 | Besecke et al. |
| 4,716,234 A | 12/1987 | Dunks et al. |
| 4,834,750 A | 5/1989 | Gupta |
| 5,290,892 A | 3/1994 | Namdaran et al. |
| 5,331,073 A | 7/1994 | Weinschenk, III et al. |
| 5,470,932 A | 11/1995 | Jinkerson |
| 5,603,774 A | 2/1997 | LeBoeuf et al. |
| 5,693,095 A | 12/1997 | Freeman et al. |
| 5,922,821 A | 7/1999 | LeBoeuf et al. |
| 6,140,438 A | 10/2000 | Ojio et al. |
| 6,241,766 B1 | 6/2001 | Liao et al. |
| 6,245,106 B1 | 6/2001 | Makker et al. |
| 6,313,187 B2 | 11/2001 | LeBoeuf et al. |
| 6,329,485 B1 | 12/2001 | Vanderbilt |
| 6,353,069 B1 | 3/2002 | Freeman et al. |
| 6,528,602 B1 | 3/2003 | Freeman et al. |
| 6,653,422 B2 | 11/2003 | Freeman et al. |
| 6,657,032 B2 | 12/2003 | Vanderbilt |
| 6,703,466 B1 | 3/2004 | Karakelle et al. |
| 6,780,899 B2 | 8/2004 | Liao et al. |
| 6,806,337 B2 | 10/2004 | Schlueter et al. |
| 6,852,793 B2 | 2/2005 | Salamone et al. |
| 6,872,793 B1 | 3/2005 | Schlueter |
| 7,585,900 B2 | 9/2009 | Cordova et al. |
| 7,605,190 B2 | 10/2009 | Moszner et al. |
| 7,652,076 B2 | 1/2010 | Schlueter et al. |
| 7,714,039 B2 | 5/2010 | Cordova et al. |
| 7,790,824 B2 | 9/2010 | Freeman |
| 7,790,825 B2 | 9/2010 | Lehman et al. |
| 7,799,845 B2 | 9/2010 | Schlueter |
| 7,847,046 B2 | 12/2010 | Schlueter et al. |
| 8,048,154 B2 | 11/2011 | Schlueter |
| 8,058,323 B2 | 11/2011 | Cordova et al. |
| 8,153,703 B2 | 4/2012 | Laredo |
| 8,207,244 B2 | 6/2012 | Laredo |
| 8,232,326 B2 | 7/2012 | Laredo |
| 8,329,097 B1 * | 12/2012 | Kunzler ........... B29D 11/00125 264/2.6 |
| 8,362,177 B1 | 1/2013 | Lehman et al. |
| 8,449,610 B2 | 5/2013 | Laredo et al. |
| 8,466,209 B2 | 6/2013 | Akinay et al. |
| 8,557,892 B2 | 10/2013 | Laredo |
| 2006/0134169 A1 | 6/2006 | Linhardt et al. |
| 2006/0275342 A1 | 12/2006 | Lindhardt et al. |
| 2007/0010883 A1 | 1/2007 | Mentak |
| 2008/0081851 A1 | 4/2008 | Benz et al. |
| 2012/0202916 A1 | 8/2012 | Laredo et al. |

OTHER PUBLICATIONS

International Searching Authority, International Search Report and Written Opinion, PCT/US2015/065506, dated Mar. 3, 2016, 11 pages.

* cited by examiner

*Primary Examiner* — Tae H Yoon
(74) *Attorney, Agent, or Firm* — Jian Zhou

(57) ABSTRACT

Acrylate-acrylamide copolymers are disclosed. They are rigid and glassy in dry state at room temperature (from about 23° C. to about 28° C.), but are soft and very deformable and have a high refractive index, a high glistening resistance and a low aging-related surface light scattering in fully hydrated state. They are particularly suitable for making wet-packed intraocular lenses (IOLs) which can be delivered through sub 2.0 mm incisions.

14 Claims, No Drawings

HYDROPHOBIC ACRYLATE-ACRYLAMIDE COPOLYMERS FOR OPHTHALMIC DEVICES

This application claims the benefit under 35 U.S.C. §119 (e) of U.S. provisional application Ser. No. 62/092,319 filed on Dec. 16, 2014, herein incorporated by reference in its entirety.

This invention is directed to hydrophobic ophthalmic device materials. In particular, this invention relates to acrylate-acrylamide copolymers which are rigid and glassy in dry state, and upon hydration, are soft and essentially free of glistenings and have a high refractive index and other desirable properties, which are especially suitable for making wet-packed intraocular lenses (IOLs) which can be delivered through sub 2.0 mm incisions.

BACKGROUND OF THE INVENTION

With advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Conventional silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than conventional silicone materials.

Acrylic materials suitable for intraocular lenses are generally soft and hydrophobic and have an equilibrium water content of less than 5% by weight. See, for example, those described in U.S. Pat. Nos. 4,834,750, 5,290,892, 5,331,073, 5,693,095, 5,922,821, 6,241,766, 6,245,106, 6,313,187, 6,353,069, 6,528,602, 6,653,422, 6,703,466, 6,780,899, 6,806,337, 6,872,793, 7,585,900, 7,652,076, 7,714,039, 7,790,824, 7,790,825, 7,799,845, 7,847,046, 8,058,323, 8,362,177, 8,466,209, 8,449,610, 8,557,892 (herein incorporated by references in their entireties). However, soft hydrophobic acrylic materials can be tacky. It is generally desirable to reduce the amount of surface tack in materials intended for use as a foldable intraocular lens. Tacky materials can be difficult to manufacture, handle, and unfold. Attempts have been made to reduce tackiness so that the lenses are easier to process or handle, easier to fold or deform, and have shorter unfolding times. For example, U.S. Pat. No. 5,603,774 discloses a plasma treatment process for reducing the tackiness of a soft acrylic material. U.S. Pat. Nos. 6,241,766; 6,245,106; 7,585,900; 7,714,039 and 8,362,177 disclose use of hydrophilic components or additives for reducing the tackiness of a soft acrylic material.

In addition, a soft hydrophobic acrylic material is susceptible to have glistenings (or microvacuoles) which are formed in vivo and can affect adversely the optical performance of intraocular lenses. Glistenings are tiny inclusions of water present within the matrix of an IOL material and are visible due to differences in refractive indices between the IOL material and water within the IOL material. It is reported that a polyethylene glycol (PEG)-containing polymerizable component (monomer and/or crosslinker) (U.S. Pat. Nos. 5,693,095, 6,353,069, and 8,449,610) can be used to improve glistening resistance of hydrophobic acrylic formulations. But, in order to minimize its adverse effects on the refractive index of acrylic materials, low amounts of PEG dimethacrylate or PEG mono-(meth)acrylate concentrations are often required. Addition of PEG dimethacrylates or PEG mono-(meth)acrylates also tends to decrease the modulus and tensile strength of the resulting copolymer.

U.S. Pat. No. 6,140,438 discloses the use of a hydrophilic monomer for improving glistening resistance of soft hydrophobic acrylic materials and the use of an alkyl (meth) acrylate for improving the flexibility and the shape restoration property of soft hydrophobic acrylic materials.

U.S. Pat. Nos. 6,329,485 and 6,657,032 disclose soft, foldable hydrogel lens materials which have a water content of approximately 5 to 30 percent by weight and are made from a composition comprising two principal monomers, one aromatic high refractive index monomer and one hydrophilic (meth)acrylate monomer (e.g., hydroxyethyl methacrylate) in an amount greater than that of the aromatic high refractive index monomer.

U.S. Pat. No. 6,852,793 discloses polymeric compositions which have a water content from 4.5 to 15 percent by weight, a relatively high refractive index of approximately 1.45 or greater, and a relatively high elongation of approximately 80 percent or greater and which are produced through the polymerization of one or more copolymers with one or more hydrophilic monomers (preferably N,N-dimethylacrylamide) and optionally one or more aromatic-based monomers, hydrophobic monomers or a combination thereof.

SUMMARY OF THE INVENTION

The present invention provides hydrophobic acrylate/ acrylamide copolymer materials suitable for making wet-packed IOLs.

The present invention is partly based on the finding that acrylamide and acrylate monomers can be copolymerized to obtain acrylate/acrylamide copolymer materials which are rigid and glassy in dry state at room temperature, but upon hydration become soft and highly-deformable (an elongation at break (or maximum strain) of greater than 90%, a Young's modulus of about 60 MPa or less, a 25% secant modulus of less than 6.0 MPa) and have a refractive index of greater than 1.50, an equilibrium water content (EWC) of less than 4.5% by weight, and a high resistance against glistenings (no bright field glistenings and minimal dark field glistenings) induced by temperature change. Because of their rigid and glassy forms in dry state at room temperature, manufacturing and handling problems associated with the surface tackiness of a hydrophobic acrylic material can be significantly reduced or eliminated. With high glistening resistance, high refractive index and high softness and deformability, the subject materials are suitable for micro-incision applications. The present invention is also partly based on the discovery that a hydrophobic acrylate/acrylamide material can be made to have minimized age-related degradation (as characterized by low surface light scattering of less than 30 CCT units (computer-compatible-tape units) after 10-years accelerated aging (90° C., 81 days in a Balanced Salt Solution, BSS, from Alcon) and minimal or no latent haze observed when heating the material from the room temperature (e.g., 23° C.) to 35° C. In this application, the term "minimal or no latent haze" or "latent haze issue being substantially reduced or eliminated" means that a hydrated material remains substantially clear (i.e.

$$\frac{T_{23} - T_{35}}{T_{23}} \leq 20\%,$$

in which $T_{23}$ and $T_{35}$ are average transmittances between 400 nm to 700 nm of the material at 23° C. and 35° C. respectively) when being heated from 23° C. to 35° C. It is believed that an acrylate/acrylamide copolymeric material with a relatively high concentration of acrylamide monomer can have a relatively-low critical solution temperature (LCST). When such a material in hydrated state is heated from room temperature to a temperature (e.g., 35° C.) above the LCST, phase separation can occur, causing the material become hazy and lose clarity. This latent haze issue can hinder the use of acrylate/acrylamide copolymers as a wet-packed IOL material. By minimizing or eliminating this latent haze issue, the subject materials are suitable for making wet-packed, glistening resistant, higher refractive index IOLs for microincision applications.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

"About" as used herein means that a number referred to as "about" comprises the recited number plus or minus 1-10% of that recited number.

"Optional" or "optionally" means that the subsequently described event or circumstance can or cannot occur, and that the description includes instances where the event or circumstance occurs and instances where it does not.

Unless indicated otherwise, all component amounts are presented on a % (w/w) basis ("wt. %").

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$ alkylamino, halogen atom (Br or Cl), and combinations thereof.

In general, the invention is directed to ophthalmic device materials which are rigid and glassy in dry state at room temperature (e.g., 23° C.), but which are soft and very deformable and have a high refractive index, a high glistening resistance and a low aging-related surface light scattering in fully hydrated state. An ophthalmic device material of the invention has minimal or no latent haze, namely this material in a fully-hydrated state remains substantially clear or clear (i.e., $$\frac{T_{23} - T_{35}}{T_{23}} \leq 20\%,$$

in which $T_{23}$ and $T_{35}$ are average transmittances between 400 nm to 700 nm of the material at 23° C. and 35° C. respectively) when being heated from 23° C. to 35° C.

An ophthalmic device material of the invention is a polymerization product of a polymerizable composition comprising:
(a) from about 20% to about 35% (preferably from about 20% to about 30%, more preferably from about 22.5% to about 27.5%) by weight of N,N dimethylacrylamide relative to the total amount of all polymerizable components,
(b) from about 51% to about 78% (preferably from about 54% to about 75%, more preferably from about 60% to about 70%) by weight of one or more aryl acrylic monomers of formula (I) relative to the total amount of all polymerizable components

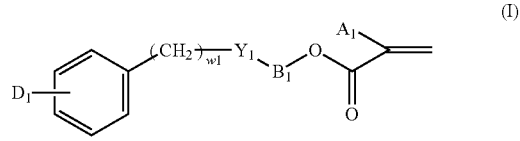

wherein $A_1$ is H or $CH_3$ (preferably H); $B_1$ is $(CH_2)_{m1}$ or $[O(CH_2)_2]_{z1}$ in which m1 is 2-6 and z1 is 1-10; $Y_1$ is a direct bond, O, S, or NR' in which R' is H, $CH_3$, $C_{n'}H_{2n'+1}$ in which n'=1-10, iso-$OC_3H_7$, $C_6H_5$, or $CH_2C_6H_5$; W1 is 0-6, provided that m1+w1≤8; and $D_1$ is H, Cl, Br, $C_1$-$C_4$ alkyl, $C_1$-$C_4$ alkoxy, $C_6H_5$, or $CH_2C_6H_5$,
(c) a polymerizable crosslinking agent,
wherein the listed components and any additional polymerizable components add up to 100% by weight, wherein the sum of the amounts of components (a) and (b) is at least about 80% by weight (preferably at least about 85% by weight, more preferably at least about 90% by weight), wherein the ophthalmic device material in a dry state has a glass transition temperature of greater than 23° C. (preferably greater than 25° C., more preferably from about 28° C. to about 40° C.), wherein the ophthalmic device material in a fully-hydrated state has: a glass transition temperature of less than 20° C. (preferably less than 18° C., more preferably less than 15° C.), a refractive index of greater than 1.50 (preferably 1.51, more preferably 1.52) measured at 589 nm and at room temperature (23±3° C.), an equilibrium water content of less than 4.5% (preferably from about 1% to about 4.2%, more preferably from about 1.5% to about 3.9%) by weight at a temperature of from 16° C. to 45° C., a glistening resistance characterized by having no bright field microvacuoles and about 10 or less microvacuoles per viewing screen, a Young's modulus of from about 1.0 MPa to about 60.0 MPa (preferably from about 2.0 MPa to about 55.0 MPa, more preferably from about 3.0 MPa to 50.0 MPa), an elongation at break of greater than 90% (preferably at least about 100%, more preferably at least about 110%), a 25% secant modulus of less than 6.0 MPa (preferably about 5.5 MPa or less, more preferably about 5.0 MPa or less), and a surface light scattering of about 30 CCT or less after 10-years accelerated aging (90° C., 81 days in a Balanced Salt Solution, BSS, from Alcon).

In accordance with the invention, a device material of the invention should have a glass transition temperature (Tg) greater than 23° C. (preferably greater than 25° C., more preferably from about 28° C. to about 40° C.) in dry state, but have a glass transition temperature of less than 20° C. (preferably less than 18° C., more preferably less than 15° C.) in a fully hydrated state.

For use in IOLs, the device materials in a fully-hydrated state of the present invention preferably exhibit sufficient strength, low stiffness, and low 25% secant modulus to allow devices made of them to be soft and highly deformable for microincision applications. Thus, an ophthalmic device material of the present invention will have: an elongation (% strain at break) of greater than 90% (preferably at least about 100%, more preferably at least about 110%); a Young's modulus of from about 1.0 MPa to about 60.0 MPa (preferably from about 2.0 MPa to about 55.0 MPa, more preferably from about 3.0 MPa to 50.0 MPa); and a 25% secant modulus of less than 6.0 MPa (preferably about 5.5 MPa or less, more preferably about 5.0 MPa or less). With such properties lenses made of such a material generally will not crack, tear or split when folded. Elongation of polymer samples is determined on dumbbell shaped tension test specimens with a 20 mm total length, length in the grip area of 11 mm, overall width of 2.49 mm, 0.833 mm width of the narrow section, a fillet radius of 8.83 mm, and a thickness of 0.9 mm. Testing is performed on samples at ambient conditions (23±2° C., 50±5% relative humidity) using an Instron Material Tester (Model No. 4442 or equivalent) with a 50 Newton load cell. The grip distance is set at 11 mm and a crosshead speed is set at 50 mm/minute and the sample is pulled until failure. The elongation (strain) is reported as a fraction of the displacement at failure to the original grip distance. The strain at break is reported as a fraction of the displacement at failure to the original grip distance. Stress at break is calculated at the maximum load for the sample, typically the load when the sample breaks, assuming that the initial area remains constant. The Young's modulus is calculated from the instantaneous slope of the stress-strain curve in the linear elastic region. The 50% secant modulus is calculated as the slope of a straight line drawn on the stress-strain curve between 0% strain and 50% strain. The 100% secant modulus is calculated as the slope of a straight line drawn on the stress-strain curve between 0% strain and 100% strain. Since materials to be tested are essentially soft elastomers, loading them into the Instron machine tends to make them buckle. To remove the slack in the material sample a pre-load is placed upon the sample. This helps to reduce the slack and provide a more consistent reading. Once the sample is pre-loaded to a desired value (typically 0.03 to 0.05 N) the strain is set to zero and the test is begun.

A device material of the present invention preferably further has an equilibrium water content of less than 4.5% (preferably from about 1% to about 4.2%, more preferably from about 1.5% to about 3.9%) by weight across the temperature range of 16-45° C. The device materials are preferably resistant to glistenings such that when equilibrated in water at 45° C. and subsequently allowed to cool to ambient temperature (approximately 22° C.) should produce no BF microvacuoles and at most 10 DF microvacuoles as detected by microscopic examination.

Aryl acrylic monomers of formula (I) can be made by methods known in the art. For example, the conjugate alcohol of the desired monomer can be combined in a reaction vessel with methyl acrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding acrylic acid to the conjugate alcohol and catalyzing with a carbodiimide or mixing the conjugate alcohol with acryloyl chloride and a base such as pyridine or triethylamine.

Suitable aryl acrylic monomers of formula (I) include, but are not limited to: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methyl benzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate; 2,4-methylphenylethyl methacrylate; 2-(4-propylphenyl)ethyl acrylate; 2-(4-propylphenyl)ethyl methacrylate; 2-(4-(1-methylethyl)phenyl) ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl) ethyl acrylate; 2-(4-cyclohexylphenyl)ethyl methacrylate; 2-(2-chlorophenyl)ethyl acrylate; 2-(2-chlorophenyl)ethyl methacrylate; 2-(3-chlorophenyl)ethyl acrylate; 2-(3-chlorophenyl)ethyl methacrylate; 2-(4-chlorophenyl)ethyl acrylate; 2-(4-chlorophenyl)ethyl methacrylate; 2-(4-bromophenyl)ethyl acrylate; 2-(4-bromophenyl)ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl)ethyl methacrylate; 2-(4-benzylphenyl)ethyl acrylate; 2-(4-benzylphenyl)ethyl methacrylate; 2-(phenylthio)ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy)ethoxy]ethyl methacrylate; or combinations thereof.

Preferred aryl acrylic monomers of formula (I) are those wherein $B_1$ is $(CH_2)_{m1}$, m1 is 2-5, $Y_1$ is nothing or O, w1 is 0 or 1, and $D_1$ is H. Most preferred are 2-phenylethyl acrylate; 3-phenylpropyl acrylate; 4-phenylbutyl acrylate; 5-phenylpentyl acrylate; 2-benzyloxyethyl acrylate; 3-benzyloxypropyl acrylate; 2-[2-(benzyloxy)ethoxy]ethyl acrylate; and their corresponding methacrylates.

The polymerizable composition for making an ophthalmic device material of the invention preferably comprises from about 51% to about 78% (preferably from about 54% to about 75%, more preferably from about 60% to about 70%) by weight of one or more aryl acrylic monomers of formula (I).

The polymerizable composition for making an ophthalmic device material of the invention preferably comprises from about 20% to about 35% (preferably from about 20% to about 30%, more preferably from about 22.5% to about 27.5%) by weight of N,-dimethylacrylamide.

The polymerizable composition for making an ophthalmic device material of the invention preferably further comprises a polymerizable cross-linking agent. The cross-linking agent may be any terminally ethylenically unsaturated compound having more than one unsaturated groups. Suitable cross-linking agents include, for example: ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; ethylene glycol diacrylate; diethylene glycol diacrylate; triethylene glycol diacrylate, tetraethylene glycol diacrylate, allyl acrylate; 1,3-propanediol diacrylate; 2,3-propanediol diacrylate; 1,6-hexanediol diacrylate; 1,4-butanediol diacrylate; N,N'-hexamethylene bisacrylamide; N,N'-hexamethylene bismethacrylamide; N,N'-dihydroxyethylene bisacrylamide; N,N'-dihydroxyethylene bismethacrylamide; N,N'-methylene bisacrylamide; N,N'-methylene bismethacrylamide; $CH_2=C(CH_3)C(=O)O-(CH_2CH_2O)_p-C(=O)C(CH_3)=CH_2$ where p=1-50; $CH_2=CHC(=O)O-(CH_2CH_2O)_p-C(=O)CH=CH_2$ where p=1-50; $CH_2=C(CH_3)C(=O)O(CH_2)_tO-C(=O)C(CH_3)=CH_2$ where t=3-20; and $CH_2=CHC(=O)O(CH_2)_tO-C(=O)CH=CH_2$ where t=3-20. A preferred cross-linking monomer is 1,6-hexanediol diacrylate, 1,4-butanediol diacrylate, or N,N'-hexamethylene bisacrylamide.

Generally, the total amount of the cross-linking component is from about 1.0% to about 6.0% by weight, preferably from about 1.5% to about 5.0% by weight, more preferably from about 2.0% to about 4.0% by weight.

The polymerizable composition for making an ophthalmic device material of the invention may further comprise one or more hydrophobic acrylamide components selected from the group consisting of N-butyl acrylamide, N-butoxymethyl acrylamide, N-methoxypropyl acrylamide, and N,N'-hexamethylene bisacrylamide (preferably from the group consisting of N-butyl acrylamide, N-butoxymethylacrylamide and N,N'-hexamethylene bisacrylamide). It is believed that a hydrophobic acrylamide component may be added to further reduce surface light scattering after 10 years of accelerating aging in a balanced salt solution (at 90° C. for 81 days).

The polymerizable composition for making an ophthalmic device material of the invention may further comprise 2-hydroxyethyl methacrylate. It is believed that 2-hydroxyethyl methacrylate may also be added to further reduce surface light scattering after 10 years of accelerating aging in a balanced salt solution (at 90° C. for 81 days).

The polymerizable composition for making an ophthalmic device material of the invention may further comprise a poly(ethylene glycol)-containing (PEG-containing) polymerizable component. It is believed that a PEG-containing polymerizable component may also be added to further reduce or eliminate latent haze issue occurred when heating an acrylate/acrylamide copolymeric material in a fully-hydrated state of the invention from room temperature (RT) to 35° C.

In accordance with the invention, a PEG-containing polymerizable component can be a linear poly(ethylene glycol) with one or two terminal polymerizable groups as described above, or a branched poly(ethylene glycol) with three or more terminal polymerizable groups as described above. Such a PEG-containing polymerizable component can be prepared according to methods known in the art from commercially available polyethylene glycols with one or more terminal functional groups (e.g., hydroxyl, amino, or carboxyl groups). Generally, a poly(ethylene glycol) with one or more hydroxyl terminal groups is dissolved in tetrahydrofuran and treated with a (meth)acrylic acid derivative such as methacryloyl chloride or methacrylic anhydride in the presence of triethylamine or pyridine. The reaction proceeds until greater than 90% of the hydroxyl groups have been converted to the corresponding acrylic or methacrylic esters. The polymer solution is filtered and the polymer is isolated by precipitation into diethyl ether. Amine and carboxylic acid terminated polyethylene glycols are functionalized in a similar manner using suitable (meth)acrylic acid derivatives.

Preferably, a PEG-containing polymerizable component used in the invention is represented by formula (II)

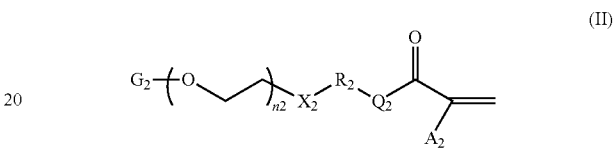

(II)

wherein: $A_2$ is H or $CH_3$; $Q_2$ and $Q_2'$ independent of each other are a direct bond, O, NH, or $C(=O)NHCH_2CH_2O$; $X_2$ and $X_2'$ independent of each other are a direct bond, O, NH, $OC(=O)NH$, or $NHC(=O)NH$ (preferably a direct bond or O); $R_2$ and $R_2'$ independent of each other are a direct bond, or $(CH_2)_p$ (preferably a direct bond); p=1-3; $G_2$ is H, $C_1$-$C_4$ alkyl, $(CH_2)_{m2}NH_2$, $(CH_2)_{m2}CO_2H$, or $R_2'$—$X_2'$-$Q_2'$-$C(=O)CA_2=CH_2$ (preferably $C_1$-$C_4$ alkyl or $R_2'$—$X_2'$-$Q_2'$-$C(=O)CA_2=CH_2$); m2=2-6; and n2=45-225 when G=H, $C_1$-$C_4$ alkyl, $(CH_2)_{m2}NH_2$, or $(CH_2)_{m2}CO_2H$; otherwise, n2=51-225 (preferably n2=45-180 when $G_2$=$C_1$-$C_4$ alkyl, otherwise, n2=51-225).

PEG-containing polymerizable components of formula (II) can be made by methods known in the art. For example, they can be prepared according to the procedures described above or as described in U.S. Pat. No. 8,449,610 (herein incorporated by reference in its entirety).

Although the total amount of the PEG-containing polymerizable component of formula (II) contained in the device materials of the present invention is from about 1% to about 5% by weight (preferably from about 2% to about 5% by weight, more preferably from about 2% to about 4% by weight), of the total amount of polymerizable components of the device materials, such amount may comprise one PEG-containing polymerizable component of formula (II) or combinations of PEG-containing polymerizable components of formula (II). The PEG-containing polymerizable component of formula (II) has a number average molecular weight of 2,000-10,000 Daltons, preferably 2,000-8,000 Daltons, more preferably 2,000-6,000 Daltons, and most preferably 2,500-6,000 Daltons.

In addition to the polymerizable components described above, the ophthalmic device materials of the present invention may also contain other ingredients, including, but not limited to, polymerizable UV-absorbers (or UV-absorbing agents), polymerizable colored dyes, siloxane monomers, and combinations thereof.

A polymerizable ultraviolet (UV) absorbing agent can also be included in the materials of the present invention. The polymerizable UV-absorbing agent can be any compound which absorbs UV light (i.e., light having a wavelength shorter than about 380 nm) and optionally high-energy-violet-light (HEVL) (i.e., light having a wavelength between 380 nm and 440 nm), but does not absorb any substantial amount of visible light having a wavelength greater than 440 nm. The UV-absorbing compound is incorporated into the monomer mixture and is entrapped in the polymer matrix when the monomer mixture is polymerized. Any suitable polymerizable UV-absorbing agents can be used in the invention. A polymerizable UV-absorbing agent used in the invention comprises a benzophenone-moiety or preferably a benzotriazole-moiety. Polymerizable benzophenone-containing UV-absorbing agents can be prepared according to procedures described in U.S. Pat. Nos. 3,162,676 and 4,304,895 (herein incorporated by reference in their entirety) or can be obtained from commercial suppliers. Polymerizable benzotriazole-containing UV-absorbing agents can be prepared according to procedures described in U.S. Pat. Nos. 3,299,173, 4,612,358, 4,716,234, 4,528,311, 8,153,703, and U.S. Pat. No. 8,232,326 (herein incorporated by reference in their entireties) or can be obtained from commercial suppliers.

Examples of preferred polymerizable benzophenone-containing UV-absorbing agents include without limitation 2-hydroxy-4-acryloxy alkoxy benzophenone, 2-hydroxy-4-methacryloxy alkoxy benzophenone, allyl-2-hydroxybenzophenone, 4-acryloylethoxy-2-hydroxybenzophenone (UV2), 2-hydroxy-4-methacryloyloxybenzophenone (UV7), or combinations thereof.

Examples of preferred polymerizable benzotriazole-containing UV-absorbing and UV/HEVL-absorbing agents include without limitation: 2-(2-hydroxy-5-vinylphenyl)-2H-benzotriazole, 2-(2-hydroxy-5-acrylyloxyphenyl)-2H-benzotriazole, 2-(2-hydroxy-3-methacrylamido methyl-5-tert octylphenyl) benzotriazole, 2-(2'-hydroxy-5-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5-methacryloxypropylphenyl) benzotriazole, 2-hydroxy-5-methoxy-3-(5-(trifluoromethyl)-2H-benzo[d][1,2,3]triazol-2-yl)benzyl methacrylate (WL-1), 2-hydroxy-5-methoxy-3-(5-methoxy-2H-benzo[d][1,2,3]triazol-2-yl)benzyl methacrylate (WL-5), 3-(5-fluoro-2H-benzo[d][1,2,3]triazol-2-yl)-2-hydroxy-5-methoxybenzyl methacrylate (WL-2), 3-(2H-benzo[d][1,2,3]triazol-2-yl)-2-hydroxy-5-methoxybenzyl methacrylate (WL-3), 3-(5-chloro-2H-benzo[d][1,2,3]triazol-2-yl)-2-hydroxy-5-methoxybenzyl methacrylate (WL-4), 2-hydroxy-5-methoxy-3-(5-methyl-2H-benzo[d][1,2,3]triazol-2-yl)benzyl methacrylate (WL-6), 2-hydroxy-5-methyl-3-(5-(trifluoromethyl)-2H-benzo[d][1,2,3]triazol-2-yl)benzyl methacrylate (WL-7), 4-allyl-2-(5-chloro-2H-benzo[d][1,2,3]triazol-2-yl)-6-methoxyphenol (WL-8), 2-{2'-Hydroxy-3'-tert-5-[3'''-(4'''-vinylbenzyloxy)propoxy]phenyl}-5-methoxy-2H-benzotriazole, phenol, 2-(5-chloro-2H-benzotriazol-2-yl)-6-(1,1-dimethylethyl)-4-ethenyl-(UVAM), 2-(2'-hydroxy-5-methacryloxyethylphenyl) benzotriazole (2-Propenoic acid, 2-methyl-, 2-[3-(2H-benzotriazol-2-yl)-4-hydroxyphenyl] ethyl ester, Norbloc), 2-{2'-Hydroxy-3'-tert-butyl-5'-[3'-methacryloyloxypropoxy]phenyl}-5-methoxy-2H-benzotriazole (UV13), 2-[2'-Hydroxy-3'-tert-butyl-5'-(3'-acryloyloxypropoxy)phenyl]-5-trifluoromethyl-2H-benzotriazole ($CF_3$—UV13), 2-(2'-hydroxy-5-methacrylamidophenyl)-5-methoxybenzotriazole (UV6), 2-(3-allyl-2-hydroxy-5-methylphenyl)-2H-benzotriazole (UV9), 2-(2-Hydroxy-3-methallyl-5-methylphenyl)-2H-benzotriazole (UV12), 2-3'-t-butyl-2'-hydroxy-5'-(3''-dimethylvinylsilylpropoxy)-2'-hydroxyphenyl)-5-methoxybenzotriazole (UV15), 2-(2'-hydroxy-5'-methacryloylpropyl-3'-tert-butyl-phenyl)-5-methoxy-2H-benzotriazole (UV16), 2-(2'-hydroxy-5'-acryloylpropyl-3'-tert-butyl-phenyl)-5-methoxy-2H-benzotriazole (UV16A), 2-Methylacrylic acid 3-[3-tert-butyl-5-(5-chlorobenzotriazol-2-yl)-4-hydroxyphenyl]-propyl ester (16-100, CAS#96478-15-8), 2-(3-(tert-butyl)-4-hydroxy-5-(5-methoxy-2H-benzo[d][1,2,3]triazol-2-yl)phenoxy)ethyl methacrylate (16-102); Phenol, 2-(5-chloro-2H-benzotriazol-2-yl)-6-methoxy-4-(2-propen-1-yl) (CAS#1260141-20-5); 2-[2-Hydroxy-5-[3-(methacryloyloxy)propyl]-3-tert-butylphenyl]-5-chloro-2H-benzotriazole; Phenol, 2-(5-ethenyl-2H-benzotriazol-2-yl)-4-methyl-, homopolymer (9Cl) (CAS#83063-87-0).

More preferably, a polymerizable UV-absorbing agent is 2-(2H-benzo[d][1,2,3]triazol-2-yl)-4-methyl-6-(2-methylallyl)phenol (oMTP), 3-[3-tert-butyl-4-hydroxy-5-(5-methoxy-2-benz[d][1,2,3]triazol-2-yl)phenoxy]propyl methacrylate (UV13), and 2-[3-(2H-benzotriazol-2-yl)-4-hydroxyphenyl]ethyl methacrylate (Norbloc 7966), or combinations thereof.

In addition to ultraviolet absorbing materials, ophthalmic devices made of the copolymers of the present invention may include colored dyes, such as the yellow dyes disclosed in U.S. Pat. Nos. 5,470,932 and 8,207,244.

The copolymers of this invention are prepared by conventional polymerization methods. For example, a mixture of one or more monomers of formula (I), N,N-dimethylacrylamide, and a cross-linking agent in the desired proportions, together with any other polymerizable components, such as a UV absorber, yellow dye, and a conventional thermal initiator (or a photointiator) is prepared. The mixture can then be introduced into a mold of desired shape, and the polymerization carried out thermally (i.e., by heating) or photochemically (i.e., by actinic radiation, e.g., UV radiation and/or visible radiation) to activate the initiator. Preferably, the mixture is cured thermally.

In a preferred embodiment, the thermal curing comprises a thermal ramp from room temperature (23±2° C.) to about 80° C. in a period time of about 20 minutes, curing at about 80° C. for about one hour, and ramping to 100° C. in about 20 minutes and curing at about 100° C. for about 2 hours. Slabs are preferably made according to this preferred curing embodiment.

In another preferred embodiment, the thermal curing comprises curing at about 100° C. for about 3 hours. IOLs are preferably made according to this preferred curing embodiment, because it is likely to provide reduced surface scattering and reduced bulk haziness.

Examples of suitable thermal initiators include: but are not limited to, azonitriles, such as 2,2'-azobis (2,4-dimethylpentanenitrile), 2,2'-azobis (2-methylpropanenitrile), 2,2'-azobis (2-methylbutanenitrile), 2,2'-azobis(isobutyronitrile) (AIBN); peroxides, such as benzoyl peroxide; peroxycarbonates, such as Perkadox 16 (bis-(4-t-butylcyclohexyl) peroxydicarbonate), and the like. A preferred initiator is AIBN, more preferably Luperox A98 (dibenzoyl peroxide). Luperox A98 is found to be better than AIBN especially for preventing pre-release without wafer plasma treatment.

Where the polymerization is carried out photochemically, a mold should be transparent to actinic radiation of a wavelength capable of initiating polymerization. Conventional photoinitiator compounds, e.g., a benzophenone-type or bisacylphosphine oxide (BAPO) photoinitiator, can also be introduced to facilitate the polymerization. Suitable photoinitiators are benzoin methyl ether, diethoxyacetophenone, a benzoylphosphine oxide, 1-hydroxycyclohexyl phenyl ketone, Darocur and Irgacur types photoinitiators (preferably Darocur 1173®, Darocur 2959® and Irgacure 819®), and Germanium-based Norrish Type I photoinitiators which are capable of initiating a free-radical polymerization under irradiation with a light source including a light in the region of about 400 to about 550 nm. Examples of benzoylphosphine initiators include 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. Examples of Germanium-based Norrish Type I photoinitiators are acylgermanium compounds described in U.S. Pat. No. 7,605,190 (herein incorporated by reference in its entirety).

Once the ophthalmic device materials of the present invention have been cured, they are extracted in a suitable solvent to remove as much of the unreacted components of the materials as possible. Examples of suitable solvents include acetone, methanol, and cyclohexane. A preferred solvent for extraction is acetone.

IOLs constructed of the disclosed ophthalmic device materials can be of any design capable of being rolled or folded into a small cross section that can fit through a relatively smaller incision. For example, the IOLs can be of what is known as a one piece or multipiece design. Typically, an IOL comprises an optic and at least one haptic. The optic is that portion which serves as the lens and the haptics are attached to the optic and are like arms which hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the ophthalmic device materials of the present invention are also suitable for use in other devices, including contact lenses, keratoprostheses, intracorneal lenses, corneal inlays or rings, and glaucoma filtration devices.

These device materials can be used to form intraocular lenses with low surface tack and high refractive indexes. Lenses made of these materials are flexible and transparent, can be inserted into the eye through a relatively small incision, and recover their original shape after having been inserted.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A polymeric ophthalmic device material, which is polymerization product of a polymerizable composition comprising
   (a) from about 20% to about 35% by weight of N,N dimethylacrylamide relative to the total amount of all polymerizable components,
   (b) from about 51% to about 78% by weight of one or more aryl acrylic monomers of formula (I) relative to the total amount of all polymerizable components

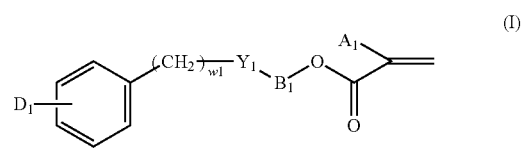

wherein $A_1$ is H or $CH_3$ (preferably H); $B_1$ is $(CH_2)_{m1}$ or $[O(CH_2)_2]_{z1}$ in which m1 is 2-6 and z1 is 1-10; $Y_1$ is a direct bond, O, S, or NR' in which R' is H, $CH_3$, $C_{n'}H_{2n'+1}$ in which n'=1-10, iso-$OC_3H_7$, $C_6H_5$, or $CH_2C_6H_5$; W1 is 0-6, provided that m1+w1≤8; and $D_1$ is H, Cl, Br, $C_1$-$C_4$ alkyl, $C_1$-$C_4$ alkoxy, $C_6H_5$, or $CH_2C_6H_5$, (c) a polymerizable crosslinking agent,
wherein the listed components and any additional polymerizable components add up to 100% by weight,
wherein the sum of the amounts of components (a) and (b) is at least about 80% by weight,
wherein the ophthalmic device material in a dried state has a glass transition temperature of greater than,
wherein the ophthalmic device material in a fully-hydrated state has: a glass transition temperature of less than 20° C., a refractive index of greater than 1.50 measured at 589 nm and at room temperature (23±3° C.), an equilibrium water content of less than 4.5% by weight at a temperature of from 16° C. to 45° C., a glistening resistance characterized by having no bright field microvacuole and about 10 or less microvacuoles per viewing screen, a Young's modulus of from about 1.0 MPa to about 60.0 MPa, an elongation at break of greater than 90%, and a 25% secant modulus of less than 6.0 MPa.

2. The ophthalmic device material according to invention 1, wherein the device material in the fully hydrated state remains substantially clear or clear (i.e., $$\frac{T_{23} - T_{35}}{T_{23}} \leq 20\%,$$

in which $T_{23}$ and $T_{35}$ are average transmittances between 400 nm to 700 nm of the material at 23° C. and 35° C. respectively) when being heated from 23° C. to 35° C.

3. The ophthalmic device material according to invention 1 or 2, wherein the device material in the fully hydrated state has a surface light scattering of about 30 CCT or less after 10-years accelerated aging (90° C., 81 days in a balanced salt solution).

4. The ophthalmic device material according to any one of inventions 1 to 3, wherein in formula (I), $B_1$ is $(CH_2)_{m1}$, m1 is 2-5, $Y_1$ is nothing or O, w1 is 0 or 1, and $D_1$ is H.

5. The ophthalmic device material according to any one of inventions 1 to 4, wherein said one or more aryl acrylic monomers are: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methylbenzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate; 2,4-methylphenylethyl methacrylate; 2-(4-propylphenyl)ethyl acrylate; 2-(4-propylphenyl)ethyl methacrylate; 2-(4-(1-methylethyl)phenyl)ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl)ethyl acrylate; 2-(4-cyclohexylphenyl)ethyl methacrylate; 2-(2-chlorophenyl)ethyl acrylate; 2-(2-chlorophenyl)ethyl methacrylate; 2-(3-chlorophenyl)ethyl acrylate; 2-(3-chlorophenyl)ethyl methacrylate; 2-(4-chlorophenyl)ethyl acrylate; 2-(4-chlorophenyl)ethyl methacrylate; 2-(4-bromophenyl)ethyl acrylate; 2-(4-bromophenyl)ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl)ethyl methacrylate; 2-(4-benzylphenyl)ethyl acrylate; 2-(4-benzylphenyl)ethyl methacrylate; 2-(phenylthio)ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy)ethoxy]ethyl methacrylate; or combinations thereof.

6. The ophthalmic device material according to any one of inventions 1 to 5, wherein said one or more aryl acrylic monomers are: 2-phenylethyl acrylate; 3-phenylpropyl acrylate; 4-phenylbutyl acrylate; 5-phenylpentyl acrylate; 2-benzyloxyethyl acrylate; 3-benzyloxypropyl acrylate; or combinations thereof.

7. The ophthalmic device material of according to any one of inventions 1 to 6, wherein the polymerizable composition comprises from about 54% to about 75% (more preferably from about 60% to about 70%) by weight of said one or more aryl acrylic monomers of formula (I).

8. The ophthalmic device material according to any one of inventions 1 to 7, wherein the polymerizable composition comprises from about 20% to about 30% (more preferably from about 22.5% to about 27.5%) by weight, of N,N dimethylacrylamide.

9. The ophthalmic device material according to any one of inventions 1 to 8, wherein the sum of the amounts of components (a) and (b) is at least about 85% by weight (more preferably at least about 90% by weight).

10. The ophthalmic device material according to any one of inventions 1 to 9, wherein the polymerizable composition comprises from about 1.0% to about 6.0% by weight, preferably from about 1.5% to about 5.0% by weight, more preferably from about 2.0% to about 4.0% by weight of the polymerizable crosslinking agent.

11. The ophthalmic device material according to invention 10, wherein the polymerizable crosslinking agent is selected from the group consisting of ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; ethylene glycol diacrylate; diethylene glycol diacrylate; triethylene glycol diacrylate, tetraethylene glycol diacrylate, allyl acrylate; 1,3-propanediol diacrylate; 2,3-propanediol diacrylate; 1,6-hexanediol diacrylate; 1,4-butanediol diacrylate; N,N'-hexamethylene bisacrylamide; N,N'-hexamethylene bismethacrylamide; N,N'-dihydroxyethylene bisacrylamide; N,N'-dihydroxyethylene bismethacrylamide; N,N'-methylene bisacrylamide; N,N'-methylene bismethacrylamide; $CH_2=C(CH_3)C(=O)O-(CH_2CH_2O)_p-C(=O)C(CH_3)=CH_2$ where p=1-50; $CH_2=CHC(=O)O-(CH_2CH_2O)_p-C(=O)CH=CH_2$ where p=1-50; $CH_2=C(CH_3)C(=O)O(CH_2)_tO-C(=O)C(CH_3)=CH_2$ where t=3-20; $CH_2=CHC(=O)O(CH_2)_tO-C(=O)CH=CH_2$ where t=3-20, and combinations thereof (preferably from the group consisting of 1,6-hexanediol diacrylate, 1,4-butanediol diacrylate, N,N'-hexamethylene bisacrylamide, and combinations thereof).

12. The ophthalmic device material according to any one of inventions 1 to 11, wherein the sum of the amounts of components (a) and (b) is at least about 85% by weight (more preferably at least about 90% by weight).

13. The ophthalmic device material according to any one of inventions 1 to 12, wherein the ophthalmic device material in the dried state has a glass transition temperature of greater than 25° C. (more preferably from about 28° C. to about 40° C.).

14. The ophthalmic device material according to any one of inventions 1 to 13, wherein the ophthalmic device material in the fully-hydrated state has a glass transition temperature of less than 18° C. (more preferably less than 15° C.).

15. The ophthalmic device material according to any one of inventions 1 to 14, wherein the ophthalmic device material in the fully-hydrated state has a refractive index of greater than 1.51 (more preferably greater than 1.52) measured at 589 nm and at room temperature (23±3° C.).

16. The ophthalmic device material according to any one of inventions 1 to 15, wherein the ophthalmic device material in the fully-hydrated state has an equilibrium water content of from about 1% to about 4.2% (more preferably from about 1.5% to about 3.9%) by weight at a temperature of from 16° C. to 45° C.

17. The ophthalmic device material according to any one of inventions 1 to 16, wherein the ophthalmic device material in the fully-hydrated state has a Young's modulus of from about 2.0 MPa to about 55.0 MPa (more preferably from about 3.0 MPa to 50.0 MPa).

18. The ophthalmic device material according to any one of inventions 1 to 17, wherein the ophthalmic device material in the fully-hydrated state has an elongation at break of at least about 100% (more preferably at least about 110%).

19. The ophthalmic device material according to any one of inventions 1 to 18, wherein the ophthalmic device material in the fully-hydrated state has a 25% secant modulus of about 5.5 MPa or less (more preferably about 5.0 MPa or less).

20. The ophthalmic device material according to any one of inventions 1 to 19, wherein the polymerizable composition further comprises at least one component selected from the group consisting of:
(i) hydroxyethyl methacrylate;
(ii) from about 1% to about 5% by weight (preferably from about 2% to about 5% by weight, more preferably from about 2% to about 4% by weight) of a poly(ethylene glycol)-containing polymerizable component of formula (II).

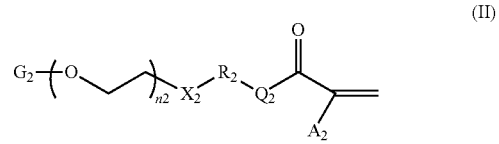

(II)

wherein: $A_2$ is H or $CH_3$; $Q_2$ and $Q_2'$ independent of each other are a direct bond, O, NH, or C(=O)

NHCH$_2$CH$_2$O; X$_2$ and X$_2$' independent of each other are a direct bond, O, NH, OC(=O)NH, or NHC(=O)NH (preferably a direct bond or O); R$_2$ and R$_2$' independent of each other are a direct bond, or (CH$_2$)$_p$ (preferably a direct bond); p=1-3; G$_2$ is H, C$_1$-C$_4$ alkyl, (CH$_2$)$_{m2}$NH$_2$, (CH$_2$)$_{m2}$CO$_2$H, or R$_2$'—X$_2$'-Q$_2$'-C(=O)CA$_2$=CH$_2$ (preferably C$_1$-C$_4$ alkyl or R$_2$'—X$_2$'-Q$_2$'-C(=O)CA$_2$=CH$_2$); m2=2-6; and n2=45-225 when G=H, C$_1$-C$_4$ alkyl, (CH$_2$)$_{m2}$NH$_2$, or (CH$_2$)$_{m2}$CO$_2$H; otherwise, n2=51-225 (preferably n2=45-180 when G$_2$=C$_1$-C$_4$ alkyl, otherwise, n2=51-225);

(iii) one or more hydrophobic acrylamide components selected from the group consisting of N-butyl acrylamide, N-butoxymethyl acrylamide, N-methoxypropyl acrylamide, and N,N'-hexamethylene bisacrylamide (preferably from the group consisting of N-butyl acrylamide, N-butoxymethylacrylamide and N,N'-hexamethylene bisacrylamide) and (iii) a combination thereof.

21. The ophthalmic device material according to invention 20, wherein the PEG-containing polymerizable component of formula (II) has a number average molecular weight of 2,000-10,000 Daltons, preferably 2,000-8,000 Daltons, more preferably 2,000-6,000 Daltons, and most preferably 2,500-6,000 Daltons.

22. The ophthalmic device material according to any one of inventions 1 to 21, wherein the polymerizable composition comprises a polymerizable UV-absorbing agent.

23. The ophthalmic device material according to any one of embodiments 1 to 21, wherein the polymerizable UV-absorbing agent is 2-(2H-benzo[d][1,2,3]triazol-2-yl)-4-methyl-6-(2-methylallyl)phenol, N-[2-[4-hydroxy-3-[2-(2-methylphenyl)diazenyl]phenyl]ethyl]methacryamide, or a combination thereof.

24. An intraocular lens comprising or consisting essentially of an ophthalmic device material according to any one of inventions 1 to 23.

25. A wet-packed intraocular lens comprising or consisting essentially of an ophthalmic device material according to any one of inventions 1 to 23.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Example 1

Argon Plasma Treatment of Molds

In order to improve pre-release performance all SN60WF molds were treated with argon plasma (AST RF Plasma chamber) prior to casting. Plasma chamber parameters were 60 Watts of forward power, 300 mTorr of pressure and a gas flow rate of 100 ml/min. The molds were treated for 15 seconds and then left on the bench for exactly 30 minutes prior to casting.

Polymer Preparation

Formulations were first purged with nitrogen for one minute and then degassed for 30 seconds under vacuum to remove any gas bubbles. They were filtered during casting through PTFE filters with a 0.2-μm pore size and, optionally, a 1.0-μm pore size and each set took approximately 10 minutes to cast. All the lenses were placed in a pre-heated oven held at 105° C. and then cured at 105° C. for 3 h. Since quick curing does not provide good quality slabs, slabs from the same formulations were ramp cured by heating the oven from ambient temperature to 70° C. in 20 min and cured for 1 h then ramped to 105° C. in 20 min and cured for 2 h. Formulations having ≤30% (parts by wt.) DMAA were extracted in acetone at room temperature under continuous stirring. Samples with ≥30% (parts by wt.) DMMA extracted in methanol. Because, samples with 35% (parts by wt.) and 40% (parts by wt.) DMAA were cracking as soon as immersed in acetone. The extraction cycle consisted of three 1 h soaks and a final rinse. The samples were then air dried for 24 hours and then vacuum dried at 70° C. for an additional 24 hours. Extractables were measured for lenses and slabs. To reduce the likelihood of a weighing error all lenses were weighed together (swelling ratio and percent extractables in methanol and acetone are recorded).

All the samples were autoclaved in vials in balanced salt solution (BSS) at 120 psi pressure and 120° C. for 30 minutes.

Pre-Release Evaluation

Prior to de-molding all SN60WF molds were examined to determine the number of lenses that had pre-released from their molds. The examination was performed by a person trained to use the standard inspection method.

Cleaning Evaluation

SN60WF lenses were de-molded and the optics punched out. They were then placed in microtubes and submitted for a cleaning assessment.

Microvacuole Testing

SN60WF lenses were subjected to a 45° C.-21° C. ΔT dark-field microvacuole test. Samples are held at 45° C. for 48 hours in BSS and then removed to room temperature (~21° C.). After 2 hours samples are inspected under the Olympus BX60 microscope at ~250× magnification in dark-field mode. Each lens is evaluated in three different areas and the highest DF MVs are counted within the approximately 1000×1000·m$^2$ imaging area. (symbol error)

Testing for the reproducibility studies were conducted a 45° C. to 37° C. ΔT bright-field microvacuole testing.

Slit Lamp Haze Evaluation

SN60WF lenses were examined by slit lamp to assess surface haze. Testing was done after the lenses had been hydrated for 24 hours in BSS. The peak haze intensity (PHI) of the posterior and anterior of each lens was determined at a 30 degree angle.

Surface Scatter and Bulk Haze Testing

In preparation for surface scatter and bulk haze testing SN60WF lenses were placed in individual crimp-top vials filled with BSS under aseptic conditions. They were aged at 90° C. for 0, 40 and 81 days, which is equivalent to 0, 5 and 10 years at 35° C. Evaluation was made by Nidek EAS 1000 Scheimpflug according to PROC-0005403.

A Scheimpflug image-capture system was set up for consistent surface-light-scattering (SLS) analysis of IOLs. A purpose-designed dark eye model was assembled that would hold the IOL being examined and that could be filled with air or with a balanced salt solution (BSS, Alcon Laboratories, Inc.) at room temperature. Images of the model eye and IOL were captured with an EAS-1000 Anterior Segment Analysis System (Nidek Co. Ltd.) using the following settings: 200 W flash, 10.00 mm slit length, 0.08 mm slit width, and a fixed camera angle position 45 degrees from the light beam path. Surface-light-scattering densitometry was measured in computer-compatible-tape (CCT) units ranging from 0 (least intense) to 255 (most intense). SLS densitometry values were measured for anterior surfaces and posterior surfaces of the IOL along the axis of a line that crossed perpendicular to the center of the IOL optic. Peak scatter intensities were measured for anterior surfaces and posterior surfaces along the axis of 3 lines within the central 3.0 mm optic zone, yielding 6 measurements per IOL, which were then averaged. Surface light scattering was measured with IOLs dry, wetted (after approximately 2 minutes in a balanced salt solution), and hydrated (after 24 hours in a balanced salt solution).

Delivery Testing

Five NG2001 netshape lenses were submitted to the IOL Delivery Testing group. These lenses were plasma treated with a one minute plasma cycle under power and pressure conditions matching the standard AcrySof cycle. Delivery testing was performed with the 1.5-mm polycarbonate NGIOL delivery system.

Injection delivery testing through a Monarch-III D cartridge was performed for 2 IOLs from each formulation as follows. A Monarch-III D cartridge was opened and filled with Viscoat. A 40D SA60AT IOL (IOLs casted in 40 Dioper molds) derived from a formulation was loaded into the cartridge in accordance with the cartridge instructions for use. The cartridge was placed into the Monarch-III D handpiece and the plunger was advanced to the screw activated point and then slowly advanced further until the IOL was engaged. The IOL was advanced through the cartridge tip and into a dish of water. The IOL was observed to determine optic unfold time and the time for the haptics to completely release from the optic.

Furthermore, the IOL was observed under a microscope at 30× magnification for any damage that occurred on injection. As well, the cartridge tip was observed for stress marks or any breakage in the crown of the tip. If no IOL damage or cartridge tip damage was observed, then the delivery was considered to be passing. IOL or tip damage meant that the delivery run was a failure.

Tensile Testing

For the determination of tensile properties of resultant materials, 8-12 mini-dogbones were cut from slab samples of each material tested, hydrated in BSS in microcentrifuge vials, and equilibrated to 18° C. in a water bath. Temperature controlled tensile testing was carried out using the Biopuls environmental chamber, which was mounted on the Instron 5943 Material Tester. The Biopuls chamber was regulated to 18° C. via circulating temperature controlled water bath. Just prior to testing mini-dogbones were removed from the 18° C. water bath and placed in the crossheads of the tensile tester. The Biopuls chamber was raised over the crossheads and samples further equilibrated for 2-min in the Biopuls chamber. Mini-dogbones were pulled at 50 mm/min rate to the breaking point to measure the tensile properties. Tensile strength (ultimate tensile stress), elongation at break (maximum strain), and Young's and secant modulus values were determined from the average of 8-12 runs per material formulation.

Yield Evaluation

Lenses were evaluated. The inspector examined each lens and determined the surface haze level and whether the lens passed surface haze and defect inspections. The surface haze level was graded as a number between 1 and 5, which equated to the following criteria: 1=none, 2=very light, 3=light, 4=medium and 5=heavy. The surface haze pass/fail criterion was based on haze uniformity and level. All grade 5 lenses were immediately considered a fail. Any grade below that could be a pass if the haze was uniform. The lens defect inspection examined any possible defect found in the optic except for surface and imbedded particulates. A lens would fail inspection if any defects were found regardless of severity.

Equilibrium Water Content

Following % extractables determination, the same samples were placed into glass vials, immersed in a Balanced Salt Solution (BSS, Alcon) and placed into a 45° C. water bath for at least 24 hours, then removed and re-weighed to determine % equilibrium water content (EWC). In a few cases the water content was determined by weighing samples before and after MV testing.

Glass Transition Temperature

The glass transition temperature (Tg) of materials in dry or fully-hydrated states was measured by differential scanning calorimetry at 10° C./minute, and was determined at the midpoint of the transition of the heat flux curve.

Refractive Index (RI)

The refractive index of the materials was measured using a Bausch & Lomb refractometer (Cat. #33.46.10) at 589 nm and 35° C. Test slab samples were hydrated in deionized water or BSS for a minimum of 24 hours, blotted dry, and then placed on the sample stage. Measurements were taken within 5 minutes of placing on stage.

Latent Haze

Latent haze was qualitatively measured using a Schott KL 2500 LCD light source. IOLs or rectangular test slabs (1×2×0.1 cm) were hydrated in BSS for a minimum of 24 hours. Hydrated samples were then immersed in a 35° C. water bath and illuminated at the highest intensity while rotating samples in the x, y, and z directions to determine the presence of latent haze. In general, hydrated materials are considered to have an unacceptable level of latent haze when the material becomes noticeably hazy in deionized water or BSS within 5 minutes at 35° C. and remains hazy for greater than 1 hour in the 35 C bath. In most cases the haze is not permanent and molecular reorientation causes the material to become clear while at 35° C. Materials having an acceptable level of latent haze generally become clear within approximately 30 minutes of heating at 35° C. Materials considered to have no latent haze show no increase in haze when placed in the 35° C. bath.

Clarity

Sample clarity was qualitatively assessed on dry and hydrated lenses using a Dolan-Jenner Fiber-Lite Fiber Optic Illuminator (model 190). Hydrated lenses were placed in the light path while rotating the samples in the x, y, and z directions to determine relative haze.

Materials

PEA=2-phenylethyl acrylate;
DMAA=N,N-dimethylacrylamide;
BDDA=1,4-butanediol diacrylate;
oMTP (0-methylallyl tinuvin p)=2-(2H-benzo[d][1,2,3]triazol-2-yl)-4-methyl-6-(2-methylallyl)phenol
AL8739=N-[2-[4-hydroxy-3-[2-(2-methylphenyl)diazenyl]phenyl]ethyl] methacryamide
AIBN=Azo-bis-(iso-butylnitrile)
Luperox A98=dibenzoyl peroxide
SN60WF=welded snap-fit polycarbonate or polypropylene IOL molds with fill holes, 20.0 diopters
Polypropylene slab molds
NG2001=netshape polycarbonate or polypropylene IOL molds, 30.0 diopters Example 2

To determine the available boundaries for the wet-pack formulation, a mixtures design with relatively broad limits were designed. The DMAA levels of 20 to 40% and BDDA levels of 2 to 4% were studied with two repeat at center point (30% DMAA with 3% BDDA). The mixture DOE was created and analyzed with the Minitab 15 Statistical Software. The 10 samples full DOE is provided in Table 1 and the responses are listed in Table 2. All formulations included 1% AIBN, 1.8% oMTP, and 0.04% AL8739. They were quick cured in an oven pre-heated to 105° C. for three hours. The same oven was used for all runs. Slabs were ramp cured as described Example 1. All the lenses were plasma treated with AcrySof cycle.

TABLE 1

| | | Conc. (by weight) | | |
|---|---|---|---|---|
| Run | Sample # | PEA (%) | DMAA (%) | BDDA (%) |
| 1 | 42-7 | 53.16 | 40 | 4 |
| 2 | 42-10 | 64.16 | 30 | 3 |
| 3 | 42-5 | 64.16 | 30 | 3 |
| 4 | 42-8 | 69.66 | 25 | 2.5 |
| 5 | 42-6 | 68.66 | 25 | 3.5 |
| 6 | 42-4 | 55.16 | 40 | 2 |
| 7 | 42-1 | 58.66 | 35 | 3.5 |
| 8 | 42-2 | 59.66 | 35 | 2.5 |
| 9 | 42-9 | 73.16 | 20 | 4 |
| 10 | 42-3 | 75.16 | 20 | 2 |

TABLE 2

| Cleaning | Extractable | Stress at break |
|---|---|---|
| Dark Field ΔT Microvacuoles | Slit lamp haze at 30° | Strain at break |
| Surface scatter at 0 and 5 yrs | Latent Haze | Young's modulus |
| Bulk haze at 0 and 5 yrs | Delivery Force | 25% Secant modulus |
| Change in EWC (RT & 35° C.) | Delivery Cosmetic Pass | Pre-release |

The 100% secant modulus measurements could not be analyzed, because some of the high DMAA and high BDDA formulations (42-1, 42-4, and 42-7) did not have any data for this response.

The cleaning, extractable, pre-release results and surface haze measurements by slit lamp are summarized in Table 3. These responses were not used in DOE, because corresponding data did not vary with composition and looked similar for all the samples. For example, all the samples passed pre-release with high success rate (>80% Pass), regardless what was the composition of the sample, because pre-release was prevented by wafer plasma treatment. Similarly, the success rate was high for particle cleaning (>80% cleaned), because all the samples were glassy in dry state made cleaning easy. Only 42-10 (one of the midpoint formulations) did show 50% cleaning, mainly due to imbedded particles. It is important to note that only particle removal and haze were studied during cleaning assessment. Other cosmetic inspections such as scratches were not evaluated. However, inspectors noted high level of scratches for all the samples. Finally, very low slit lamp haze was measured for all the formulations except 42-9 (30° Haze was ~10±9 PHI). However, only one surface of one of the lenses had very high haze ~17 PHI resulted in a high average value with a high standard deviation. Otherwise, when high value is treated as an outlier, then the average haze would be 2±2 PHI. The 5 year surface scattering (SS) and bulk haze (BH) results were not available when the time DOE was run. However, this did not create a significant difference in DOE result, because all the samples had low SS and BH except one of the lowest composition corner (42-3, 20% DMAA with 2% BDDA) had about 20 CCT SS and around 7 PHI BH. This particular sample had also the highest latent haze, which was used in DOE analysis, as reported in Table 4.

TABLE 3

| ID | U.Cle. (n = 10) | D.Cle. | P.rel. (% Pass, n = 40) | Extra. (Gen 1) (%) | S.H.(n = 2) Slit lamp 30° (PHI) | S.S. T = 0 yr | B.H. T = 0 yr | S.S. T = 5 yr | B.H. T = 5 yr |
|---|---|---|---|---|---|---|---|---|---|
| 42-1 | 90 | 100 | 97.4 | 2.3 ± 0.08 | 0.5 ± 0.9 | 6.3 ± 3.5 | 2.3 ± 1.3 | 6.7 ± 2.8 | 0.8 ± 1.0 |
| 42-2 | 80 | 100 | 92.5 | 2.44 ± 0.04 | 1 ± 0.8 | 5.8 ± 4 | 2.5 ± 1.6 | 15.1 ± 11 | 1.6 ± 1.0 |
| 42-3 | 80 | 80 | 80.95 | 2.48 ± 0.06 | 1.8 ± 2.2 | 7.4 ± 3.8 | 2 ± 1.1 | 19.8 ± 4.4 | 7.1 ± 4.1 |
| 42-4 | 100 | 100 | 94 | 2.3 ± 0.11 | 1.5 ± 0.5 | 8.2 ± 4.6 | 1.5 ± 1.5 | 15.2 ± 18.4 | 0.7 ± 0.8 |
| 42-5 | 70 | 90 | 87.5 | 2.3 ± 0.4 | 2.2 ± 2.6 | 4.7 ± 2.2 | 2 ± 1.6 | 8.1 ± 3.8 | 1.5 ± 0.9 |
| 42-6 | 55.6 | 88.9 | 87.5 | 2.1 ± 0.18 | 3.1 ± 2.2 | 7.1 ± 3.5 | 2.7 ± 1.4 | 8 ± 2.3 | 1.9 ± 1.6 |
| 42-7 | 67 | 100 | 92.5 | 2.8 ± 0.44 | 4 ± 3.6 | 4.6 ± 3.1 | 2.6 ± 1.3 | 8.7 ± 4.8 | 1.9 ± 1.0 |
| 42-8 | 50 | 90 | 97.5 | 2.32 ± 0.13 | 5.2 ± 4 | 12.3 ± 11.5 | 1.9 ± 1.1 | 8.7 ± 1.6 | 3.1 ± 1.4 |
| 42-9 | 60 | 90 | 95 | 1.86 ± 0.2 | 10 ± 9 | 6.4 ± 4.1 | 1.3 ± 1.3 | 7.8 ± 2.2 | 1.7 ± 1.2 |
| 42-10 | 50 | 50 | 95 | 2.23 ± 0.17 | 1.7 ± 2.2 | 8.5 ± 5 | 2.3 ± 1.7 | 6.6 ± 2.9 | 2.3 ± 1.3 |

U.Cle. = Ultrasonic cleaning;

D.Cle. = Digital cleaning;

P.rel. = pre-release;

Extra. = Extraction;

S.H. = surface haze;

S.S. = surface scattering;

B.H. = bulk haze

The DOE was created and analyzed with the Minitab 15 Statistical Software. DOE regression analysis results are summarized in Table 4. Dark field MVs, latent haze, change in the water content between ambient temperature and 35° C., delivery force and cosmetic and tensile properties were found to be significantly depend upon composition and used as responses. Key results are summarized in Table 5. Latent haze observation was scaled as 0 being none, 0.5 being a tint of haze, 2 being slight haze and 10 matches to intense haze. Interactions between PEA*DMAA and PEA*BDDA are found to be significant but DMAA*BDDA not.

TABLE 4

| Response | $r^2$ (adj) | p (regression) | p (linear) | p (quad) | Significant Interactions |
|---|---|---|---|---|---|
| ΔEWC (23° C.-35° C.) | 82.92 | 0.009 | 0.496 | 0.129 | PEA*DMAA |
| DF MVs | 75.42 | 0.022 | 0.056 | 0.021 | PEA*DMAA, PEA*BDDA |
| Latent Haze | 80.51 | 0.012 | 0.046 | 0.062 | PEA*BDDA |
| Delivery Force (N) | 92.92 | 0.001 | 0.101 | 0.031 | PEA*DMAA, PEA*BDDA |
| % Delivery Cosmetic Pass | 86.67 | 0.005 | 0.006 | 0.011 | PEA*DMAA |
| Stress at Break (MPa) | 96.86 | 0.000 | 0.022 | 0.413 | None |
| Strain at Break (%) | 96.59 | 0.000 | 0.007 | 0.118 | PEA*DMAA, PEA*BDDA |
| Young's Modulus (MPa) | 87.46 | 0.004 | 0.160 | 0.110 | PEA*BDDA |
| 25% Secant Modulus (MPa) | 94.71 | 0.001 | 0.397 | 0.111 | PEA*BDDA |

TABLE 5

| ID | Dark Field MVs (n = 3) | Latent Haze (n = 2) | ΔEWC (ppm) (23° C.-35° C.) | % Post Delivery Cosmetic Pass (n = 5) | Delivery Force (N) | % Strain | Stress (MPa) | Young's Mod (MPa) | 25% Secant Mod (MPa) |
|---|---|---|---|---|---|---|---|---|---|
| 42-1 | 2 | 2 | −12.2 | 60 | 12.1 ± 0.9 | 93 ± 6.5 | 3 ± 0.4 | 12.1 ± 1.4 | 2.9 ± 0.1 |
| 42-2 | 1 | 10 | −12.6 | 80 | 10.4 ± 1.9 | 126 ± 6.5 | 3.4 ± 0.3 | 10.6 ± 1.2 | 2.3 ± 0.02 |
| 42-3 | 30 | 0 | 4.3 | 60 | 14.5 ± 1.6 | 184 ± 7.5 | 7.2 ± 0.8 | 55 ± 2.8 | 3.3 ± 0.06 |
| 42-4 | 6 | 10 | −16.7 | 0 | 10.3 ± 2.3 | 102 ± 8 | 1.6 ± 0.2 | 20.7 ± 5 | 1.8 ± 0.04 |
| 42-5 | 5 | 2 | −15 | 100 | 13.3 ± 1.3 | 120 ± 4.1 | 4.5 ± 0.4 | 22 ± 0.8 | 3 ± 0.04 |
| 42-6 | 0 | 0.5 | −2.9 | 100 | 18.8 ± 1.2 | 137 ± 7.5 | 7.1 ± 0.9 | 56.6 ± 2.3 | 4.6 ± 0.1 |
| 42-7 | 6 | 0.5 | −15 | 20 | 12.9 ± 1.9 | 56.5 ± 3.2 | 1.5 ± 0.1 | 2.3 ± 0.03 | 2.9 ± 0.04 |
| 42-8 | 3 | 0.5 | −5.6 | 100 | 12.9 ± 0.9 | 163 ± 5.6 | 6.2 ± 0.4 | 52.6 ± 2.3 | 3.6 ± 0.07 |
| 42-9 | 4 | 0 | 0 | 100 | 22.3 ± 0.6 | 121 ± 1 | 7.6 ± 0.1 | 71 ± 2 | 5.5 ± 0.06 |
| 42-10 | 4 | 2 | −15 | 80 | 14 ± 0.9 | 124 ± 4.3 | 4.7 ± 0.4 | 21.8 ± 1 | 3 ± 0.06 |

The DOE resulted in the selected optimized formulation in Table 6.

TABLE 6

| Component | PEA | DMAA | BDDA | oMTP | AL8739 | AIBN |
|---|---|---|---|---|---|---|
| Composition (%) | 69.8 | 24.6 | 3.8 | 1.80 | 0.04 | 1.00 |

The results for the optimized formulation shown in table are as follows. EWC % is 3.5% by weight; the hydrated refractive index is 1.54; and the glass transition temperature in fully-hydrated state is 11.5° C.

Example 3

The selected optimized formulation shown in Table 6 above was repeated three identical batches to determine if the formulation was robust. During repeat study, the formulation batches were divided into two and one group was thermal quick cured while the second half was thermal ramp cured to study effect of curing conditions on the optimized wet-pack formulation. In addition Delivery test was carried out on both the plasma treated and not treated samples from the same batch to study whether plasma treatment necessary for desired unfolding behavior of the lenses.

Table 7 lists the delivery results. For reference, delivery force of DOE run for formulation 42-6 (Example 2) is 18.8±1.2 N. The maximum force range for baseline (empty cartridge) was 16.1-16.2N.

TABLE 7

| | Delivery No Plasma Treatment (n = 5) | | | Delivery with Plasma Treated IOLs (n = 5) | | |
|---|---|---|---|---|---|---|
| Sample ID | Delivery Force (N) | Unfold time (s) | Cosmetic Pass (%) | Delivery Force (N) | Unfold time (s) | Cosmetic Pass (%) |
| 74-1QC | 19.3 ± 1.1 | 1-2 | 75 | 21.4 ± 2.7 | 1 | 80 |
| 74-2QC | 20.2 ± 2.4 | 1 | 100 | 22.7 ± 2.6 | 1 | 80 |

TABLE 7-continued

| | Delivery No Plasma Treatment (n = 5) | | | Delivery with Plasma Treated IOLs (n = 5) | | |
|---|---|---|---|---|---|---|
| Sample ID | Delivery Force (N) | Unfold time (s) | Cosmetic Pass (%) | Delivery Force (N) | Unfold time (s) | Cosmetic Pass (%) |
| 74-3QC | 21.1 ± 2.3 | 2-60+ (1 lens) | 80 | 22.6 ± 1.5 | 1-2 | 80 |
| 74-1RC | 19.4 ± 0.2 | 1-2 | 100 | 21.5 ± 3.3 | 1 | 80 |
| 74-2RC | 19.5 ± 3.1 | 1 | 100 | 20 ± 1.4 | 1 | 80 |
| 74-3RC | 20.6 ± 2.7 | 1 | 60 | 19.4 ± 2.9 | 2 | 100 |

All the repeats of optimized formulation had consistent delivery force around 20N, which is maximum value for the funnel criteria. However, no cosmetic issue and no haptic sticking were noted even with not plasma treated samples except only one not plasma treated lens out of 30 IOLs did show 60+s unfolding time. No nozzle damage was observed.

Optimized Wet-Pack repeats were also subjected to cleaning, latent haze, pre-release, surface scattering, bulk and surface haze, gravimetric extractable and dark field MVs tests and results are summarized in Table 8. Pre-release was no issue with the 15s Ar-Plasma treated Gen1 wafers. No latent haze was observed for all the repeats. Cleanability was usually better than 60% for 4 of the 6 lots. 2 lots did fail cleaning test mostly because of embedded particles and extreme scratches. Extractables were about 2% when extracted in methanol for all the quick and ramp cured samples. MV performance was good. Unexpectedly, relatively high surface haze was measured for all the samples by slit lamp measurements at 30°. A typical AcrySof lens has a surface haze level of 18 PHI. However, n=6 IOLs from a fourth lot (74-4RC and QC) did show 3.8 and 3.2 PHI surface haze, respectively. In addition all the 10 of the optimization DOE samples had very low surface haze.

Tensile mechanical properties of all the repeats were found similar to each other and also found comparable to closest DOE sample (42-6, Example 2) reported in Table 9.

TABLE 9

| ID | Stress at break (MPa) | Strain at Break (%) | Young's Mod (MPa) | 25% Secant Mod (MPa) | 100% Secant Mod (MPa) |
|---|---|---|---|---|---|
| Tensile Testing, Hydrated at room temperature | | | | | |
| 74-1RC | 7.4 ± 0.7 | 130 ± 6.3 | 76.5 ± 5 | 5.0 ± 0.1 | 4.4 ± 0.1 |
| 74-2RC | 8.1 ± 0.9 | 134 ± 6.7 | 74.6 ± 6.1 | 4.9 ± 0.1 | 4.4 ± 0.1 |
| 74-3RC | 7.4 ± 0.6 | 131 ± 4 | 76 ± 5 | 4.9 ± 0.1 | 4.3 ± 0.2 |
| 42-6 | 7.1 ± 0.9 | 137 ± 8 | 57 ± 2.3 | 4.6 ± 0.1 | 3.8 ± 0.1 |
| Tensile Testing, hydrated at 35° C. | | | | | |
| 74-1RC | 1.64 ± 0.2 | 60.3 ± 6.2 | 19.3 ± 3.3 | 2.8 ± 0.1 | N/A |
| 74-2RC | 1.60 ± 0.2 | 55.7 ± 4.8 | 18 ± 6.4 | 2.9 ± 0.1 | N/A |
| 74-3RC | 1.40 ± 0.1 | 52 ± 3.9 | 21.3 ± 6.2 | 2.8 ± 0.1 | N/A |
| 42-6 | | | N/A | | |

TABLE 8

| ID | U.Cle. (n = 10) | After D.cle. | P.rel. (% Pass, n = 48*) | Extra. (Gen 1) (%) | D.F. MVs# (n = 3) | S.H. (n = 2) Slit lamp 30° (PHI) | S.S (CCT) T = 0 yr | B.H. T = 0 yr | S.S. (CCT) T = 10 yr | B.H. T = 10 yr |
|---|---|---|---|---|---|---|---|---|---|---|
| 74-1QC | 60 | 70 | 90 | 2.2 ± 0.1 | 3.3 ± 2.5 | 13.5 ± 3.1 | 4.9 ± 2.6 | 1.8 ± 1.1 | 8.1 ± 2.3 | 2.0 ± 1.0 |
| 74-2QC | 40 | 70 | 93 | 2.2 ± 0.2 | 6.3 ± 2.5 | 35.7 ± 20 | 8.5 ± 10.9 | 0.3 ± 0.6 | 8.4 ± 2.9 | 2.7 ± 1.2 |
| 74-3QC | 30 | 30 | 96 | 1.8 ± 0.2 | 4.3 ± 1.5 | 25.3 ± 12 | 10.9 ± 7.6 | 0.4 ± 0.6 | 5.7 ± 3.2 | 2.0 ± 1.1 |
| 74-1RC | 50 | 80 | 90 | 2.1 ± 0.2 | 4.3 ± 4 | 10.4 ± 6.8 | 6.2 ± 2.3 | 2.1 ± 1.2 | 11.9 ± 2.9 | 3.1 ± 2.4 |
| 74-2RC | 20 | 40 | 89 | 2.1 ± 0.2 | 5.7 ± 3.1 | 18.9 ± 16 | 6.2 ± 3.8 | 0.8 ± 0.7 | 23.9 ± 6.7 | 3.3 ± 1.5 |
| 74-3RC | 50 | 60 | 96 | 1.9 ± 0.1 | 1.7 ± 0.6 | 15 ± 3.4 | 5.4 ± 2.5 | 0.9 ± 1.0 | 13.4 ± 2.7 | 2.6 ± 1.6 |

U.Cle. = Ultrasonic cleaning;

D.Cle. = Digital cleaning;

P.rel. = pre-release;

Extra. = Extraction;

S.H. = surface haze;

S.S. = surface scattering;

B.H. = bulk haze;

D.F. = dark field;

*Ar-plasma treatment;

average spots

Based on all the data above, it was found that the optimized formulation is repeatable, robust and passed all the criteria.

Example 4

Higher and lower DMAA (24-30%) and lower crosslinker (1.5-3.5%) levels were studied compared to optimized formulation shown in Table 6 to soften the material in order to reduce delivery force (see Table 10 for the formulations). In general, only a slight decrease in modulus was measured in the operation room temperature range (16° C.-25° C.) for the higher DMAA and lower crosslinker samples. Table 10 reports delivery force measurements and latent haze assessments. Some of the modified formulations such as 42-11, 17-3&4 and 42-8 (one of the DOE sample) had lower delivery force than 20N. These modified formulations were then delivered by two surgeons. Neither surgeon was able to differentiate the delivery performance of optimized versus modified formulations.

TABLE 10

| Sample | Formulation | Max Delivery Force (N) | Latent Haze |
|---|---|---|---|
| Center Point | 30 DMAA/3.0 BDDA | 13.6 ± 1.6 | Slight |
| Optimized (Historical 3-lot data) 74-1, −2, −3 | 24.6 DMAA/3.8 BDDA | 20 ± 1.8 | None |
| Optimized form 74-9 | 24.6 DMAA/3.8 BDDA | 18.4 ± 1.0 | None |
| Modified-I 42-11 | 27 DMAA/3.5 BDDA | 18.2 ± 1.6 | Very slight |
| Modified-II 17-4 | 28 DMAA/3.5 BDDA | 16.9 ± 1.4 | Very slight |
| Modified-III 17-5 | 28 DMAA/1.5 BDDA | N/A | Intense |
| Modified-IV 17-1 | 29 DMAA/3.5 BDDA | N/A | slight |
| Modified-V 17-3 | 24 DMAA/1.5 BDDA | 16 ± 0.7 | Very slight |
| DOE-42-8 | 25 DMAA/2.5BDDA | 13 ± 1 | Very slight |

Example 5

An initiator screening study was also conducted on optimized wet-pack formulation. As a result of the initiator screening, Luperox A98 (dibenzoyl peroxide, Mwt=242) was found to be better initiator for the wet-pack formulation compared to AIBN especially when pre-release without mold treatment concerned.

With the optimized formulation and the initiator selected, the team moved forward with selection of an optimized cure and initiator composition. As there were only two factors, cure temperature and initiator concentration, 2 DOEs were carried out with full factorial design. First DOE run for ramp curing and the other was for quick curing while the Luperox A98 concentration varied (0.75%-1.25%-1.75%). The DOEs are provided in Table 11 and the responses are listed in Table 12. For ramp curing the oven was programmed to go designated T (75, 85 or 95° C.) from ambient temperature in 20, 34 and 38 min, respectively for 1 h followed by 2 h at 100° C. For quick curing, the oven was preheated to the designated temperature (75, 88 or 101° C.) for 1 h followed by 2 hour at 100° C. None of the molds were argon plasma treated to measure the real pre-release as part of the formulation and curing conditions.

TABLE 11

| Run | Cure Temperature (° C.) | Initiator Concentration (%) |
|---|---|---|
| 1-1 | 85 | 1.25 |
| 1-2 | 75 | 0.75 |
| 1-3 | 95 | 1.75 |
| 1-4 | 85 | 1.75 |
| 1-5 | 95 | 0.75 |
| 1-6 | 85 | 0.75 |
| 1-7 | 95 | 1.25 |
| 1-8 | 75 | 1.75 |
| 1-9 | 75 | 1.25 |
| 2-1 | 88 | 0.75 |
| 2-2 | 101 | 1.25 |
| 2-3 | 101 | 1.75 |
| 2-4 | 88 | 1.25 |
| 2-5 | 88 | 1.75 |
| 2-6 | 75 | 1.25 |
| 2-7 | 101 | 0.75 |
| 2-8 | 75 | 1.75 |
| 2-9 | 75 | 0.75 |

TABLE 12

| Pre-release | Surface Haze by Slit lamp |
|---|---|
| Extractable % Cosmetic and Haze (FLE) Latent Haze | Tensile properties Surface Scatter/Bulk Haze (t = 0, 5 and 10 yr) |

The DOEs were created and analyzed with the Minitab 16 statistical software program. The key analysis results for ramp cure and quick cure DOEs are provided in Tables 13 and 14, respectively. Cosmetic FLE inspection results were used in three categories: cosmetic visual haze level, % cosmetic pass and % cosmetic pass when scratches were not considered as failure. In addition, some lenses were failed because of bubble formation when quick cured at relatively high temperature 101° C.

TABLE 13

| | DOE RUN # | | | | | | | | |
|---|---|---|---|---|---|---|---|---|---|
| | 1-2 | 1-5 | 1-6 | 1-1 | 1-7 | 1-9 | 1-3 | 1-4 | 1-8 |
| Pre-release (%) | 96.9 | 40.6 | 71.9 | 78.1 | 34.4 | 71.9 | 15.6 | 31.2 | 37.5 |
| Extractable (%) | 2.49 | 2.55 | 2.45 | 2.35 | 2.38 | 2.55 | 2.58 | 2.52 | 2.55 |
| Cosmetic Haze | 3 | 1 | 3.5 | 6 | 1 | 3.5 | 3 | 3.5 | 3 |
| Cosmetic Pass (%) | 0 | 48.1 | 0 | 44.4 | 0 | 0 | 0 | 0 | 0 |
| Cosmetic pass w/o Scratch (%) | 30.8 | 48.1 | 57.7 | 44.4 | 0 | 59.3 | 3.7 | 3.1 | 21.4 |
| Slit Lamp Haze | 5.8 | 10.1 | 11.2 | 5.2 | 6.4 | 10.8 | 10.9 | 4.2 | 11.8 |
| Stress (MPa) | 5.4 | 5.4 | 5.4 | 5.2 | 5.7 | 5.4 | 5.9 | 5.9 | 5.8 |
| Strain (%) | 116 | 118 | 117 | 116 | 119 | 114 | 118 | 118 | 115 |

TABLE 13-continued

| | DOE RUN # | | | | | | | | |
|---|---|---|---|---|---|---|---|---|---|
| | 1-2 | 1-5 | 1-6 | 1-1 | 1-7 | 1-9 | 1-3 | 1-4 | 1-8 |
| Young's modulus (MPa) | 39.2 | 38.1 | 40.6 | 40.4 | 42.2 | 41.1 | 45.1 | 44.3 | 43.5 |
| 100% Secant Modulus (MPa) | 4 | 3.9 | 4 | 3.9 | 4.1 | 4.2 | 4.3 | 4.3 | 4.4 |
| Latent Haze | clear | clear | clear | clear | clear | clear | clear | clear | clear |

TABLE 14

| | DOE RUN # | | | | | | | | |
|---|---|---|---|---|---|---|---|---|---|
| | 2-1 | 2-2 | 2-3 | 2-4 | 2-5 | 2-6 | 2-7 | 2-8 | 2-9 |
| Pre-release (%) | 50 | 75 | 65.6 | 62.5 | 53.1 | 71.9 | 84.4 | 40.6 | 84.4 |
| Extractable (%) | 2.58 | 2.42 | 2.49 | 2.25 | 2.31 | 2.47 | 2.51 | 2.46 | 2.48 |
| Cosmetic Haze | 3 | 3 | 1 | 3 | 3 | 3 | 1 | 3 | 1 |
| Cosmetic Pass (%) | 19.2 | 11.1 | 0 | 3.7 | 0 | 0 | 0 | 0 | 0 |
| Cosmetic pass w/o Scratch (%) | 50 | 55.6 | 0 | 59.3 | 0 | 15.4 | 0 | 29.6 | 0 |
| Slit Lamp Haze | 15.3 | 13.5 | 10.2 | 19.8 | 9.5 | 10.1 | 5.6 | 6.5 | 6.4 |
| Stress (MPa) | N/A | N/A | N/A | N/A | N/A | 5.6 | N/A | 5.9 | 5.5 |
| Strain (%) | N/A | N/A | N/A | N/A | N/A | 116 | N/A | 117 | 117 |
| Young's modulus (MPa) | N/A | N/A | N/A | N/A | N/A | 44.4 | N/A | 45.3 | 39.4 |
| 100% Secant Modulus (MPa) | N/A | N/A | N/A | N/A | N/A | 4.2 | N/A | 4.4 | 4.1 |
| Latent Haze | clear | clear | clear | clear | clear | clear | clear | clear | clear |

Table 15 summarizes results of Pareto Charts for both DOEs, whether the given response are significantly affected by the response within 95% confidence level. Note that quick curing does not produce good quality slabs at 88° C. and above.

TABLE 15

| Response | A98 Conc | Temp | A98*T |
|---|---|---|---|
| Ramp Cure DOE | | | |
| Pre-release | Significant | Significant | Significant |
| Extractable | Not significant | Not significant | Not significant |
| Cosmetic Haze | Not significant | Not significant | Not significant |
| Cosmetic Pass | N/A | N/A | N/A |
| Cosmetic Pass w/o scratch | Not significant | Not significant | Not significant |
| Haze by Slit Lamp | Not significant | Not significant | Not significant |
| Stress | Significant | Not significant | Not significant |
| Strain | Not significant | Significant | Not significant |
| Young's Mod | Significant | Not significant | Not significant |
| Quick Cure DOE | | | |
| Pre-release | Not significant | Not significant | Not significant |
| Extractable | Not significant | Not significant | Not significant |
| Cosmetic Haze | Not significant | Not significant | Not significant |
| Cosmetic Pass | Not significant | Not significant | Not significant |
| Cosmetic Pass w/o scratch | Not significant | Not significant | Not significant |
| Haze by Slit Lamp | Not significant | Not significant | Not significant |
| Stress | N/A | N/A | N/A |
| Strain | N/A | N/A | N/A |
| Young's Mod | N/A | N/A | N/A |

Table 16 summarizes cure DOEs optimum conditions. Ramp Cure DOE provided that 0.75% A98 and heating to 77.5° C. would be desired condition. While the quick cure DOE results were mostly statistically insignificant, the data showed that combining a higher cure temperature around 98° C. and 1% initiator concentration led to somewhat better performance. However, some lenses were lost because of bubble formation curing at 101° C. The 5 year surface scattering (SS) and bulk haze (BH) results have just been come out and presented in Tables 17 and 18. Both ramp curing and quick curing did show similar SS and BH results. Based on these results, ramp curing is recommended from ambient to 77.5° C. in 20 min for three hours and an initiator concentration of 0.75% A98. Mainly because, better slit lamp haze was measured and it produced slabs compared to quick curing, which may result in bubble formation. Otherwise the rest of the properties were found similar.

TABLE 16

| Cure Type | Optimized A98 Concentration (%) | Optimized Cure Temperature (° C.) |
|---|---|---|
| Ramp Cure | 0.75 | 77.5 |
| Quick Cure | 1.0 | 98.0 |

TABLE 17

| Sample | Ramp Cure DOE | | Quick Cure DOE | |
|---|---|---|---|---|
| Init/T-RC (T-QC)* | SS (CCT) T = 0 yr | SS (CCT) T = 5 yr | SS (CCT) T = 0 yr | SS (CCT) T = 5 yr |
| 0.75/75 (75) | 5.9 ± 3.1 | 9.2 ± 2.3 | 4.3 ± 1.1 | 6.6 ± 2.4 |
| 0.75/85 (88) | 5.2 ± 2.8 | 7.4 ± 1.2 | 6.7 ± 3.6 | 6.4 ± 1.9 |
| 0.75/100 (101) | 4.3 ± 1.7 | 10.4 ± 0.3 | 3.5 ± 2.5 | 10.3 ± 2.0 |
| 1.25/75 (75) | 7.8 ± 3.4 | 11.6 ± 0.9 | 4.9 ± 1.9 | 9.5 ± 1.2 |
| 1.25/85 (88) | 5.1 ± 3.1 | 11.1 ± 0.8 | 5.8 ± 3.0 | 11.1 ± 3.5 |
| 1.25/100 (101) | 5.3 ± 3 | 9.4 ± 2.5 | 3.9 ± 1.9 | 7.8 ± 1.1 |
| 1.75/75 (75) | 8.1 ± 4.0 | 12.2 ± 0.9 | 5.8 ± 2.7 | 11.3 ± 0.4 |
| 1.75/85 (88) | 6.9 ± 4.3 | 10.2 ± 1.9 | 9.2 ± 5.2 | 13.6 ± 1.9 |
| 1.75/100 (101) | 4.8 ± 1.7 | 11.1 ± 0.7 | 7.3 ± 3.4 | 11.8 ± 0.8 |

[Init/T-RC (T-QC)* = % A98/ramp to T (pre-heated oven T)]

TABLE 18

| Sample | Ramp Cure DOE | | Quick Cure DOE | |
|---|---|---|---|---|
| Init/T-RC (T-QC) | BH (CCT) T = 0 yr | BH (CCT) T = 5 yr | BH (CCT) T = 0 yr | BH (CCT) T = 5 yr |
| 0.75/75 (75) | 1.8 ± 1.4 | 3.6 ± 0.5 | 1.0 ± 0.7 | 3.4 ± 1.6 |
| 0.75/85 (88) | 1.7 ± 1.3 | 2.7 ± 1.3 | 1.6 ± 0.7 | 2.7 ± 1.3 |
| 0.75/100 (101) | 1.9 ± 1.1 | 4.4 ± 1.3 | 1.6 ± 1.0 | 4.2 ± 1.3 |
| 1.25/75 (75) | 2.0 ± 0.9 | 14.0 ± 2.6 | 2.0 ± 1.1 | 6.1 ± 0.5 |
| 1.25/85 (88) | 2.9 ± 1.3 | 6.4 ± 1.3 | 1.3 ± 1.1 | 7.8 ± 2.8 |

TABLE 18-continued

| Sample | Ramp Cure DOE | | Quick Cure DOE | |
|---|---|---|---|---|
| Init/T-RC (T-QC) | BH (CCT) T = 0 yr | BH (CCT) T = 5 yr | BH (CCT) T = 0 yr | BH (CCT) T = 5 yr |
| 1.25/100 (101) | 2.9 ± 0.6 | 5.4 ± 0.7 | 2.4 ± 0.9 | 4.4 ± 0.7 |
| 1.75/75 (75) | 3.3 ± 1.0 | 8.8 ± 1.3 | 2.3 ± 1.3 | 10.8 ± 0.2 |
| 1.75/85 (88) | 1.8 ± 1.2 | 7.6 ± 0.8 | 4.2 ± 1.5 | 10.6 ± 1.5 |
| 1.75/100 (101) | 3.1 ± 1.1 | 10.6 ± 0.8 | 4.0 ± 0.7 | 11.1 ± 0.8 |

We claim:

1. A polymeric ophthalmic device material, which is polymerization product of a polymerizable composition comprising
(a) from about 20% to about 35% by weight of N,N dimethylacrylamide relative to the total amount of all polymerizable components,
(b) from about 60% to about 70% by weight of one or more aryl acrylic monomers of formula (I) relative to the total amount of all polymerizable components

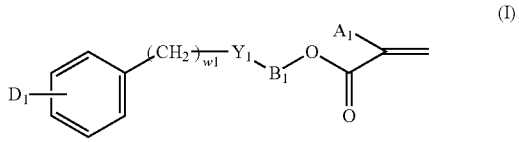

wherein $A_1$ is H or $CH_3$; $B_1$ is $(CH_2)_{m1}$ or $[O(CH_2)_2]_{z1}$ in which m1 is 2-6 and z1 is 1-10; $Y_1$ is a direct bond, O, S, or NR' in which R' is H, $CH_3$, $C_{n'}H_{2n'+1}$ in which n'=1-10, iso-$OC_3H_7$, $C_6H_5$, or $CH_2C_6H_5$; W1 is 0-6, provided that m1+w1≤8; and $D_1$ is H, Cl, Br, $C_1$-$C_4$ alkyl, $C_1$-$C_4$ alkoxy, $C_6H_5$, or $CH_2C_6H_5$,
(c) a polymerizable crosslinking agent,
wherein the listed components and any additional polymerizable components add up to 100% by weight,
wherein the sum of the amounts of components (a) and (b) is at least 90% by weight,
wherein the ophthalmic device material in a dried state has a glass transition temperature of from about 28° C. to about 40° C.,
wherein the ophthalmic device material in a fully-hydrated state has: a glass transition temperature of less than 20° C., a refractive index of greater than 1.50 measured at 589 nm and at room temperature (23±3° C.), an equilibrium water content of from about 1.5% to about 3.9% by weight at a temperature of from 16° C. to 45° C., a glistening resistance characterized by having no bright field microvacuole and about 10 or less microvacuoles per viewing screen, a Young's modulus of from about 1.0 MPa to about 60.0 MPa, an elongation at break of greater than 90%, and a 25% secant modulus of less than 6.0 MPa.

2. The ophthalmic device material of claim 1, wherein the device material in the fully hydrated state remains substantially clear or clear, as characterized by having $$\frac{T_{23} - T_{35}}{T_{23}} \le 20\%,$$

in which $T_{23}$ and $T_{35}$ are average transmittances between 400 nm to 700 nm of the material at 23° C. and 35° C. respectively when being heated from 23° C. to 35° C.

3. The ophthalmic device material of claim 2, wherein the device material in the fully hydrated state has a surface light scattering of about 30 CCT or less after 10-years accelerated aging.

4. The ophthalmic device material of claim 2, wherein in formula (I), $B_1$ is $(CH_2)_{m1}$, m1 is 2-5, $Y_1$ is nothing or O, w1 is 0 or 1, and $D_1$ is H.

5. The ophthalmic device material of claim 4, wherein said one or more aryl acrylic monomers are: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methylbenzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate; 2,4-methylphenylethyl methacrylate; 2-(4-propylphenyl)ethyl acrylate; 2-(4-propylphenyl)ethyl methacrylate; 2-(4-(1-methylethyl)phenyl)ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl)ethyl acrylate; 2-(4-cyclohexylphenyl)ethyl methacrylate; 2-(2-chlorophenyl)ethyl acrylate; 2-(2-chlorophenyl)ethyl methacrylate; 2-(3-chlorophenyl)ethyl acrylate; 2-(3-chlorophenyl)ethyl methacrylate; 2-(4-chlorophenyl)ethyl acrylate; 2-(4-chlorophenyl)ethyl methacrylate; 2-(4-bromophenyl)ethyl acrylate; 2-(4-bromophenyl)ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl)ethyl methacrylate; 2-(4-benzylphenyl)ethyl acrylate; 2-(4-benzylphenyl)ethyl methacrylate; 2-(phenylthio)ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy)ethoxy]ethyl methacrylate; or combinations thereof.

6. The ophthalmic device material of claim 5, wherein said one or more aryl acrylic monomers are: 2-phenylethyl acrylate; 3-phenylpropyl acrylate; 4-phenylbutyl acrylate; 5-phenylpentyl acrylate; 2-benzyloxyethyl acrylate; 3-benzyloxypropyl acrylate; 2-[2-(benzyloxy)ethoxy]ethyl acrylate; or combinations thereof.

7. The ophthalmic device material of claim 6, wherein the polymerizable composition comprises from about 1.0% to about 6.0% by weight of the polymerizable crosslinking agent.

8. The ophthalmic device material of claim 7, wherein the polymerizable crosslinking agent is selected from the group consisting of ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; ethylene glycol diacrylate; diethylene glycol diacrylate; triethylene glycol diacrylate, tetraethylene glycol diacrylate, allyl acrylate; 1,3-propanediol diacrylate; 2,3-propanediol diacrylate; 1,6-hexanediol diacrylate; 1,4-butanediol diacrylate; N,N'-hexamethylene bisacrylamide; N,N'-hexamethylene bismethacrylamide; N,N'-dihydroxyethylene bisacrylamide; N,N'-dihydroxyethylene bismethacrylamide; N,N'-methylene bisacrylamide; N,N'-methylene bismethacrylamide; $CH_2$=$C(CH_3)C(=O)O$—$(CH_2CH_2O)_p$—$C(=O)C(CH_3)$=$CH_2$ where p=1-50;

$CH_2=CHC(=O)O-(CH_2CH_2O)_p-C(=O)CH=CH_2$ where p=1-50; $CH_2=C(CH_3)C(=O)O(CH_2)_tO-C(=O)C(CH_3)=CH_2$ where t=3-20; $CH_2=CHC(=O)O(CH_2)_tO-C(=O)CH=CH_2$ where t=3-20, and combinations thereof.

9. The ophthalmic device material of claim 5, wherein the polymerizable composition comprises from about 1.0% to about 6.0% by weight of the polymerizable crosslinking agent.

10. The ophthalmic device material of claim 9, wherein the polymerizable crosslinking agent is selected from the group consisting of ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; ethylene glycol diacrylate; diethylene glycol diacrylate; triethylene glycol diacrylate, tetraethylene glycol diacrylate, allyl acrylate; 1,3-propanediol diacrylate; 2,3-propanediol diacrylate; 1,6-hexanediol diacrylate; 1,4-butanediol diacrylate; N,N'-hexamethylene bisacrylamide; N,N'-hexamethylene bismethacrylamide; N,N'-dihydroxyethylene bisacrylamide; N,N'-dihydroxyethylene bismethacrylamide; N,N'-methylene bisacrylamide; N,N'-methylene bismethacrylamide; $CH_2=C(CH_3)C(=O)O-(CH_2CH_2O)_p-C(=O)C(CH_3)=CH_2$ where p=1-50; $CH_2=CHC(=O)O-(CH_2CH_2O)_p-C(=O)CH=CH_2$ where p=1-50; $CH_2=C(CH_3)C(=O)O(CH_2)_tO-C(=O)C(CH_3)=CH_2$ where t=3-20; $CH_2=CHC(=O)O(CH_2)_tO-C(=O)CH=CH_2$ where t=3-20, and combinations thereof.

11. The ophthalmic device material of claim 2, wherein the polymerizable composition further comprises at least one component selected from the group consisting of:
(i) hydroxyethyl methacrylate;
(ii) from about 1% to about 5% by weight of a poly(ethylene glycol)-containing polymerizable component of formula (II)

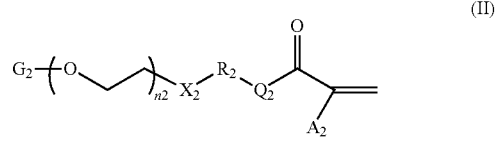

(II)

wherein: $A_2$ is H or $CH_3$; $Q_2$ and $Q_2'$ independent of each other are a direct bond, O, NH, or $C(=O)NHCH_2CH_2O$; $X_2$ and $X_2'$ independent of each other are a direct bond, O, NH, $OC(=O)NH$, or $NHC(=O)NH$; $R_2$ and $R_2'$ independent of each other are a direct bond, or $(CH_2)_p$; p=1-3; $G_2$ is H, $C_1$-$C_4$ alkyl, $(CH_2)_{m2}NH_2$, $(CH_2)_{m2}CO_2H$, or $R_2'$—$X_2'$-$Q_2'$-$C(=O)CA_2=CH_2$; m2=2-6; and n2=45-225 when G=H, $C_1$-$C_4$ alkyl, $(CH_2)_{m2}NH_2$, or $(CH_2)_{m2}CO_2H$; otherwise, n2=51-225; and
(iii) a combination thereof.

12. The ophthalmic device material of claim 11, wherein the poly(ethylene glycol)-containing polymerizable component of formula (II) has a number average molecular weight of 2,000-10,000 Daltons.

13. The ophthalmic device material of claim 1, wherein the polymerizable composition comprises a polymerizable UV-absorbing agent.

14. An intraocular lens comprising an ophthalmic device material of claim 1.

* * * * *